US008313475B2

(12) United States Patent
Clarke et al.

(10) Patent No.: US 8,313,475 B2
(45) Date of Patent: Nov. 20, 2012

(54) LIQUID DISPENSER

(75) Inventors: Ian Clarke, Callaghan (AU); Kenneth Arthur Logan, Callaghan (AU); Paul Christopher Dastoor, Callaghan (AU)

(73) Assignee: Keystone Product Developments Pty Ltd (AU)

( * ) Notice: Subject to any disclaimer, the term of this patent is extended or adjusted under 35 U.S.C. 154(b) by 773 days.

(21) Appl. No.: 10/533,842

(22) PCT Filed: Nov. 5, 2002

(86) PCT No.: PCT/AU02/01499
§ 371 (c)(1),
(2), (4) Date: May 4, 2005

(87) PCT Pub. No.: WO03/039433
PCT Pub. Date: May 15, 2003

(65) Prior Publication Data
US 2006/0015084 A1    Jan. 19, 2006

(30) Foreign Application Priority Data
Nov. 5, 2001   (AU) ........................................ PR8679

(51) Int. Cl.
*A61B 19/00*    (2006.01)
*A61M 37/00*    (2006.01)
(52) U.S. Cl. ........................ 604/403; 604/141
(58) Field of Classification Search .......... 604/403–416, 604/19, 21, 30, 140–144
See application file for complete search history.

(56) References Cited

U.S. PATENT DOCUMENTS

| 4,033,378 A | * | 7/1977 | Pauliukonis | 137/614.19 |
| 4,666,430 A | * | 5/1987 | Brown et al. | 604/141 |
| 5,106,374 A | | 4/1992 | Apperson | 604/140 |
| 5,163,909 A | | 11/1992 | Stewart | 604/140 |
| 5,207,645 A | * | 5/1993 | Ross et al. | 604/141 |
| 5,954,696 A | | 9/1999 | Ryan | 604/141 |
| 6,062,429 A | | 5/2000 | West | 222/95 |

FOREIGN PATENT DOCUMENTS

CA    2083555    *   5/1994
(Continued)

OTHER PUBLICATIONS

Supplementary Partial European Search Report for corresponding European Patent Application No. 02774156.0 dated Jul. 27, 2007.
International Search Report for PCT/AU02/01499 dated Dec. 12, 2002.

*Primary Examiner* — Philip R Wiest
(74) *Attorney, Agent, or Firm* — Ostrolenk Faber LLP

(57) ABSTRACT

The present invention relates to an apparatus for controlled rate dispensing of a liquid contained in a flexible bag, said apparatus including a chamber adapted to contain the flexible bag containing the liquid, an outlet from the chamber adapted to receive an outlet conduit communicating with the interior of the flexible bag, a source of gas arranged to apply pressure to at least part of the exterior walls of the flexible bag, and a pressure regulator arranged to control the pressure applied to said exterior walls, whereby pressure applied to said exterior walls causes liquid to be dispensed from the flexible bad through the outlet conduit at a controlled rate. A method of delivering liquid at a controlled rate using the apparatus of the present invention is also described.

11 Claims, 5 Drawing Sheets

FOREIGN PATENT DOCUMENTS

| | | | |
|---|---|---|---|
| DE | 10319874 | | 8/2004 |
| FR | 2850582 | | 8/2004 |
| GB | 2165312 | * | 4/1986 |
| GB | 2165312 A | * | 4/1986 |
| WO | WO 9604029 | | 2/1996 |
| WO | 2005/011778 | | 2/2005 |

* cited by examiner

LIQUID DISPENSER

CROSS REFERENCE TO RELATED APPLICATION

The present application is a 35 U.S.C. §371 national phase conversion of PCT/AU2002/01499 filed 5 Nov. 2002.

The PCT International Application was published in the English language.

This invention relates to a liquid dispenser and has been devised particularly though not solely for low flow rate dispensing of medical liquids for intravenous drip applications.

There are many situations where it is desirable to be able to provide a controlled low flow rate delivery of a liquid from a compact, portable and reliable device. In particular, there are many medical situations in which it is desirable to supply liquids such as intravenous drip fluids for patients in a reliable and easily regulated device which at the same time is compact and portable so that it is convenient for the patient to use.

In the past, low flow rate dispensing devices, and in particular intravenous drip supply devices, have been provided in a number of different formats including the conventional gravity feed bag which is typically hung from a support rack located above the patient. Such devices are cumbersome for the patient to use, requiring the feeding of a tube from a fixed and elevated situation to the point of dispensing on the patient and furthermore they are not readily portable.

Alternative portable devices for the supply of intravenous drip fluids for patients have included a round bag with a spring loaded container which is expensive to manufacture, incorporates a screw mechanism which is difficult to load for some patients, and which does not always ensure a linear delivery of fluid. Other devices include an elastomer device incorporating a container with a balloon which is fully disposable and typically loaded by a hypodermic syringe. These devices are expensive to use due to their "one use" configuration, have limitations on the volume of fluid contained (typically 50 milliliters) and must be filled by a health care professional. There are also syringe drivers, which are typically powered by electric motors and again are expensive both to provide and maintain.

There are also many other non-medical applications such as the supply of lubricating fluids to machinery, the dosing of antibacterial fluids into cooling towers or air conditioning systems, and other similar applications which require a compact and reliable apparatus for controlled rate low flow dispensing of liquids.

Accordingly, the present invention provides an apparatus for controlled rate dispensing of a liquid contained in a flexible bag, said apparatus including a chamber adapted to contain the flexible bag containing the liquid, an outlet from the chamber adapted to receive an outlet conduit communicating with the interior of the flexible bag, a source of gas arranged to apply pressure to at least part of the exterior walls of the flexible bag, and a pressure regulator arranged to control the pressure applied to said exterior walls, whereby pressure applied to said exterior walls causes liquid to be dispensed from the flexible bag through the outlet conduit at a controlled rate.

In one embodiment of the invention, the chamber is a substantially gas-tight chamber, the outlet from the chamber is adapted to seal the outlet conduit to the chamber, and the source of gas is arranged to supply gas under pressure to the interior of the chamber, thereby applying pressure to the exterior walls of the flexible bag. In this embodiment, the pressure regulator is preferably arranged to regulate the flow of gas from the source of gas to the chamber.

In an alternative embodiment of the invention, the source of gas is connected to an inflatable bladder such that, in use, the inflatable bladder is in contact with an exterior wall of the flexible bag. An advantage of this arrangement is that it obviates the need for a substantially gas-tight chamber having seals. This type of chamber is relatively easy to manufacture and eliminates the potential problem of gas leaking through seals in the chamber.

In this alternative embodiment the inflatable bladder is preferably also in contact with an inside wall of the chamber, in use. Preferably, the inflatable bladder comprises an inflatable sock adapted to wrap around at least part of the flexible bag. Such an arrangement is advantageous, because it applies a substantially even pressure to the exterior walls of the flexible bag and allows a substantially constant rate of flow of liquid from the bag. Preferably, in this alternative embodiment, the pressure regulator is arranged to regulate flow of gas from the source of gas to the inflatable bag.

Preferably, the source of gas comprises a pressure vessel of pre-compressed gas.

Alternatively, the source of gas comprises a reservoir pressurised by a pump.

Preferably, the flexible bag is a medical supply bag of the type used to supply intravenous drip fluids for patients.

Preferably, the flexible bag comprises a so-called Baxter bag.

Preferably, the apparatus is arranged to dispense liquids at a controlled low flow rate.

The low flow rate may be, for example, less than 100 milliliters per hour (ml/hr), less than 50 ml/hr, less than 25 ml/hr, or less than 10 ml/hr.

Preferably, the chamber is provided in a relatively flat cuboidal configuration having a depth significantly less than the length or width of the chamber.

Preferably, the pressure vessel and gas regulator are located alongside the chamber in a common housing arranged such that the pressure vessel and gas regulator are contained within the depth of the housing. This arrangement allows convenient use and/or transportation of the apparatus.

Preferably, the housing is provided with a support strap adapting the housing to be worn by a patient.

The present invention further provides a method of delivering liquid from a flexible bag at controlled rate, said method including the steps of providing an apparatus as defined in any one of the preceding claims, setting the pressure regulator to a predetermined pressure, and applying pressure to at least part of the exterior walls of the flexible bag.

Notwithstanding any other forms that may fall within its scope, two preferred forms of the invention will now be described by way of example only with reference to the accompanying drawings in which.

Figure 1:
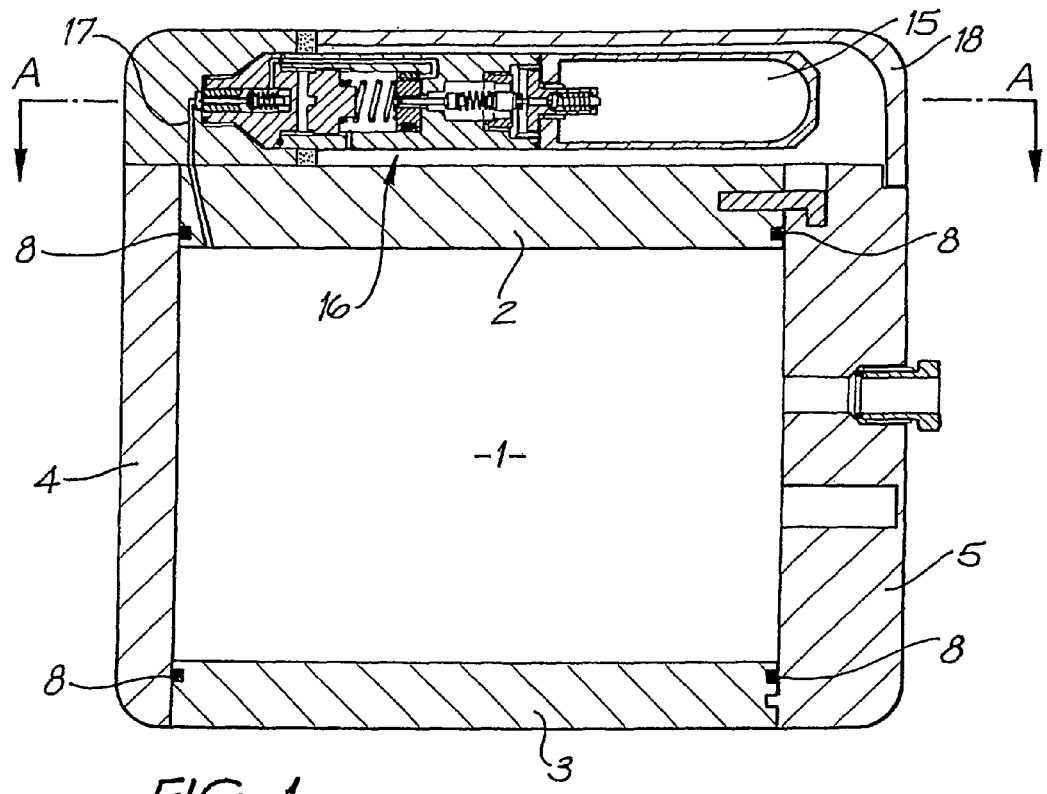
FIG. 1 is a cross-sectional plan view through a first liquid dispensing apparatus according to the invention.

In a first preferred form of the invention, a liquid dispensing apparatus particularly designed for dispensing intravenous drip fluids to patients is constructed as follows, although it will be appreciated that the apparatus can be used for other applications and provided in other configurations.

The apparatus comprises a substantially gas tight cuboidal chamber 1 typically defined by solid plastics components formed for example of acrylic or polycarbonate materials. The plastics components define side walls 2 and 3 to the chamber, an end wall 4, and a removable cap wall 5. The chamber is completed by face plate portions 6 and 7 and formed into a gas tight configuration by the use of O-ring seals 8.

Figure 4:
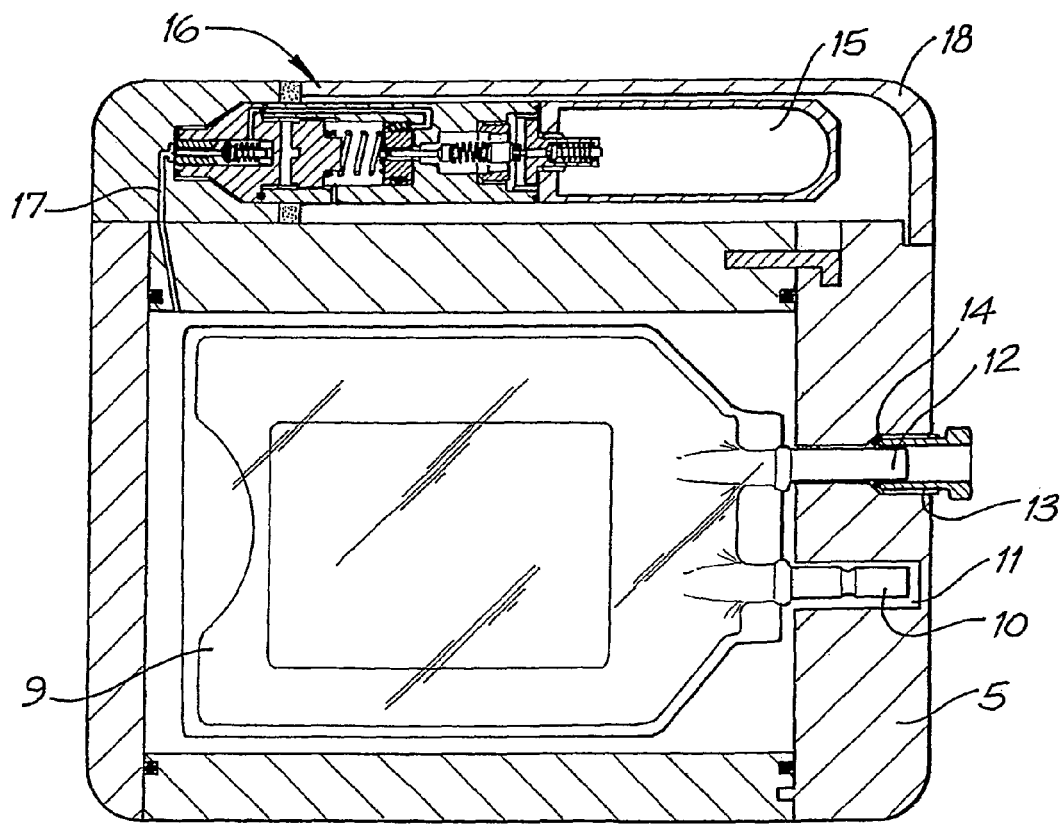
FIG. 4 is a similar view to FIG. 1 showing a flexible bag containing liquid in place within the chamber of the apparatus.
Figure 5:
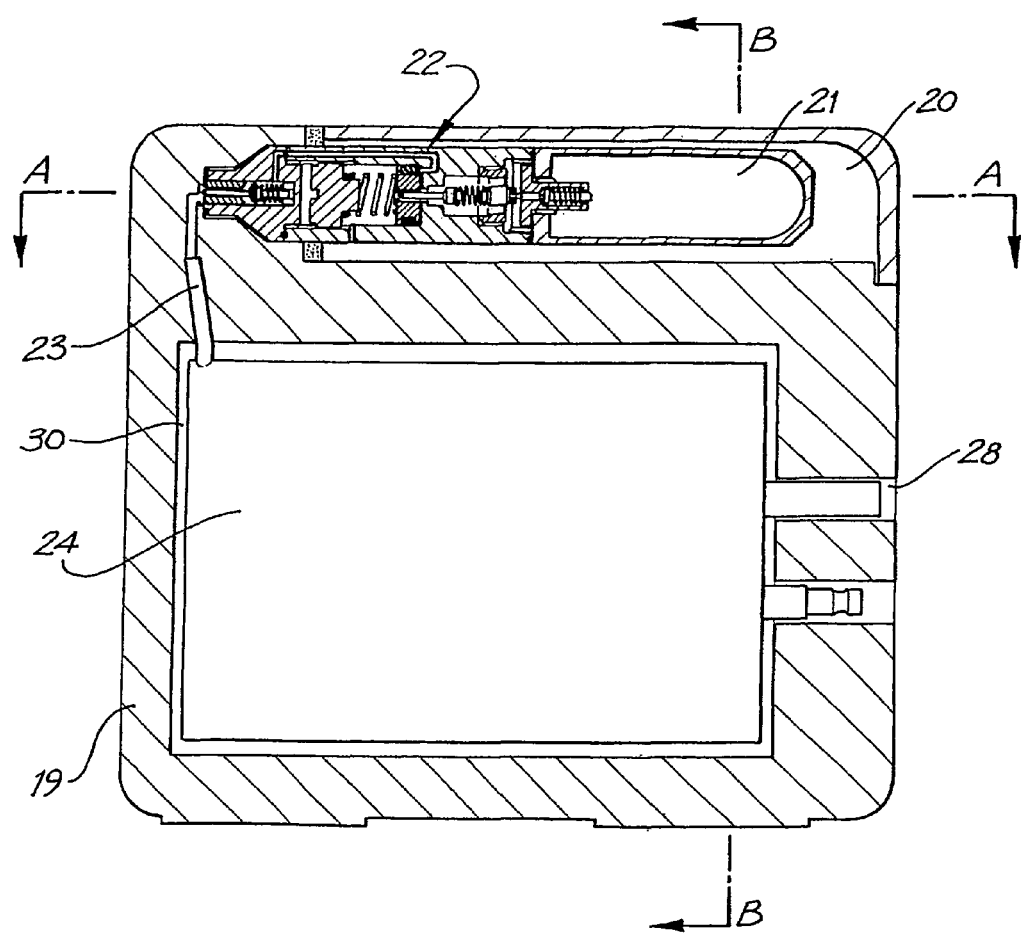
FIG. 5 is a cross-sectional plan view through a second liquid dispensing apparatus according to the invention.
Figure 6:
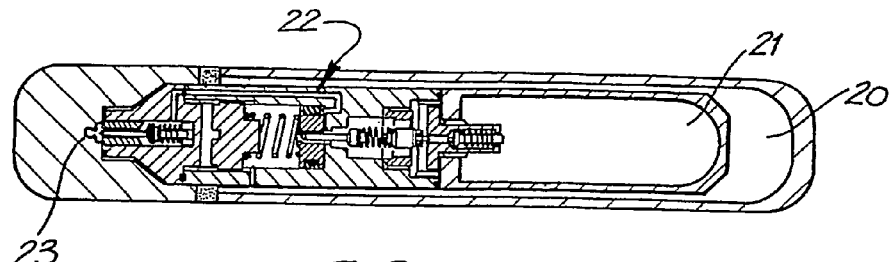
FIG. 6 is a cross-sectional elevation along the line AA of FIG. 5.

The chamber 1 is sized to receive a full medical supply bag such as a Baxter bag shown in FIG. 4 at 9.

The Baxter bag is typically provided with a filling conduit 10 which is accommodated within a recess 11 in the cap 5 and an outlet conduit 12 which is located within an outlet 13 from the chamber 1 which in turn is provided with a seal 14 arranged to seal the outer periphery of the outlet conduit 12 to the cap 5, thus maintaining the gas tight nature of the chamber 1.

The outlet 12 may be connected to the ultimate dispensing point e.g. to an intravenous drip needle by way of the commonly known flexible tube (not shown).

The apparatus is further provided with a source of gas in the form of a pressure vessel 15 which is similar to the type used to provide pressurised gas such as $CO_2$ or air for an inflatable life jacket or other similar uses. There is also provided a pressure regulator 16 arranged to regulate the supply of gas from the pressure vessel 15 and feed that gas into chamber 1 through conduit 17 located within the housing such that the gas pressure within chamber 1 is maintained at a relatively constant and predetermined level.

The pressure regulator 16 may take any known form, although typically comprises the compression spring controlled piston device shown in FIGS. 1 and 4 using needle valves to regulate and control the gas supply pressure. It will be appreciated however that many different types of pressure regulators are well known and could be substituted for the regulator shown at 16.

Figure 2:
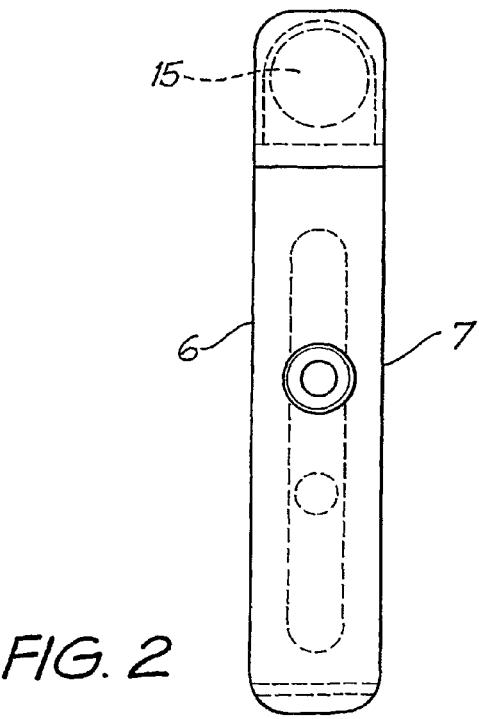
FIG. 2 is a front view of the apparatus shown in FIG. 1.
Figure 3:
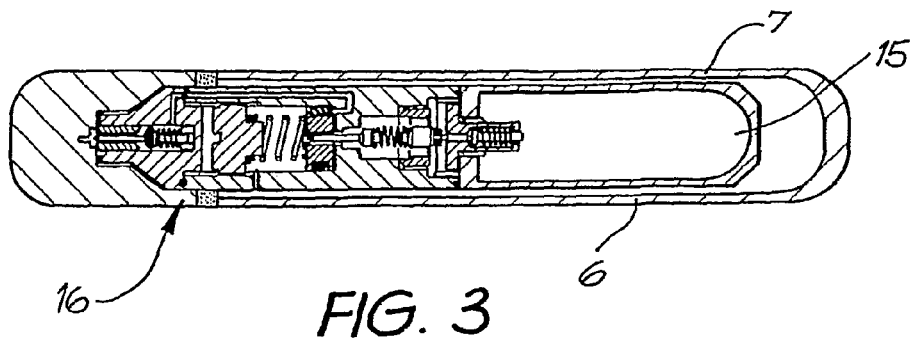
FIG. 3 is a cross-sectional elevation on the line AA of FIG. 1.

It is an advantageous feature of the preferred embodiment of the invention that both the pressure vessel 15 and the gas regulator 16 can be located alongside the chamber 1 as shown in FIGS. 1 and 4 with the supply and regulation devices contained within the overall depth of the housing as can be clearly seen in FIG. 2. This results in a compact and easy to handle apparatus while still retaining good access to the mounting for the pressure vessel 15, enabling the pressure vessel to be easily changed and replaced as needed.

In use, the pressure regulator 16 is either pre-calibrated, or adjusted, to provide a supply of gas through conduit 17 into chamber 1 calculated to maintain a predetermined gas pressure within chamber 1 regardless of the volume of fluid contained at any point in time in the bag 9. In this manner, the dispensing force on the liquid within the bag 9 is constant over the full range of the bag, from fill to empty, ensuring a constant flow rate of fluid from the bag through the outlet conduit 12, against the back pressure of any regulating device that may be installed in the supply line connected to the outlet conduit. This enables an extremely accurate flow rate of liquid to be achieved over the entire dispensing range from the bag 9.

It is a further feature of the invention, that the gas pressure within the chamber 1 enables all of the liquid within the bag to be dispensed, again providing accurate measurement of total fluids dispensed to a patient, and providing efficient utilisation of all liquid within the bag.

Because the housing formed by the members 2, 3, 4, 5, 6, and 7, and the further housing 18 supporting the pressure regulator and pressure vessel, are arranged in a relatively flat cuboidal configuration having a depth significantly less than the length or width of the chamber, the resulting apparatus is very compact and easy to wear by a patient. The apparatus can easily be provided with a support strap in the form of either a waistband or a shoulder strap (not shown), adapting the housing to be worn by a patient in a position where it is extremely easy and convenient to lead a supply tube from the outlet conduit 12 to the dispensing point on the body of the patient.

Although the apparatus has been described with the source of gas as being a pressure vessel of pre-compressed gas, it will be appreciated that other alternatives could be used such as a hand pump pressurised reservoir contained within or connected to the apparatus. Similarly, other configurations of pressure regulator could be used either to regulate the supply between the source of gas and the chamber as shown in the accompanying drawings or as a pressure relief valve in the chamber to control the build up of pressure within the chamber.

In a second preferred form of the invention, and with reference to FIGS. 5-9, a housing 19 is formed from plastics components, such as acrylic or polycarbonate materials. The housing 19 is similar in design to the housing shown in FIGS. 1-4 However, the housing lacks the O-ring seals 8 shown in FIG. 1. The housing 19 includes a recess 20 and a chamber 30. The recess accommodates a source of gas, in the form of a pressure vessel 21, and an associated pressure regulator 22. The pressure vessel 21 and pressure regulator are typically of the same or similar design to those described above in connection with the first preferred form of the invention. Furthermore, as in the first preferred form, the recess 20 allows convenient and compact design of the liquid dispenser.

A conduit 23 connects the pressure regulator 22 to an inflatable bladder 24, which takes the form of an elongate gas sock. The inflatable bladder 24 is accommodated in the chamber 30 and substantially fills the space defined by the chamber 30. The pressure regulator 22 is used to set the pressure inside the inflatable bladder 24 to a constant and predetermined pressure. The inflatable bladder 24 may be formed from any inflatable material, such as plastics or rubber. Such materials will be well known to the skilled person and are typically used in the manufacture of balloons and the like.

Figure 7:
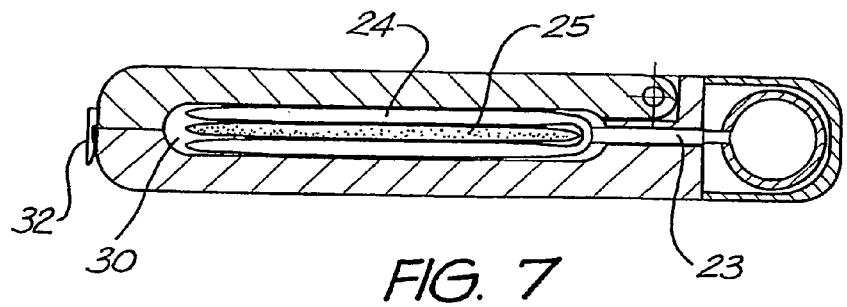
FIG. 7 is a cross-sectional elevation along the line BB of FIG. 5.
Figure 9:
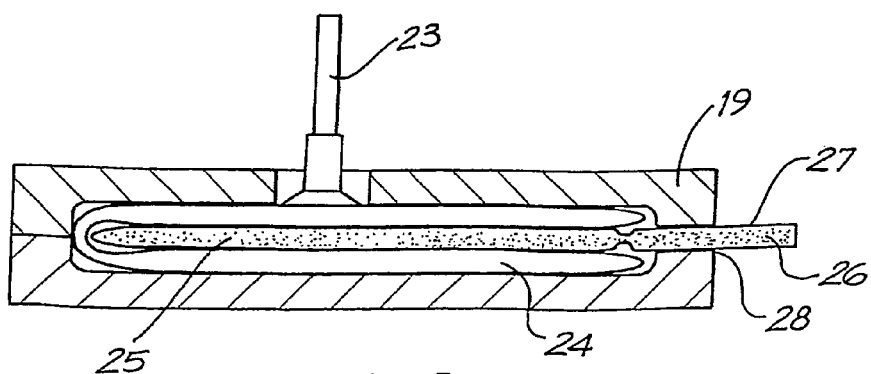
FIG. 9 is a schematic cross-sectional elevation of the second liquid dispensing apparatus according to the invention.

Referring now to FIGS. 7 and 9, the gas sock 24 is wrapped around a substantial part of a bag 25, which will typically be a Baxter bag, as exemplified in FIG. 4. In the embodiment shown in FIGS. 7 and 9, the bladder 24 is in contact with both the inside wall of the chamber 30 and the exterior walls of the bag 25. Hence, when the bladder 24 is inflated by gas delivered from the conduit 23, it squeezes the bag 25 and forces liquid 26 out of the bag through a conduit 27. The conduit 27 passes through an outlet 28 in the housing 19 and communicates with the interior of the bag 25. An advantage of this second preferred form of the invention is that the outlet 28 need not seal the conduit 27 to the chamber 19. All the gas used to force liquid from the bag 25 is contained in the bladder 24, obviating the need for gas-seals in the chamber.

Figure 8:
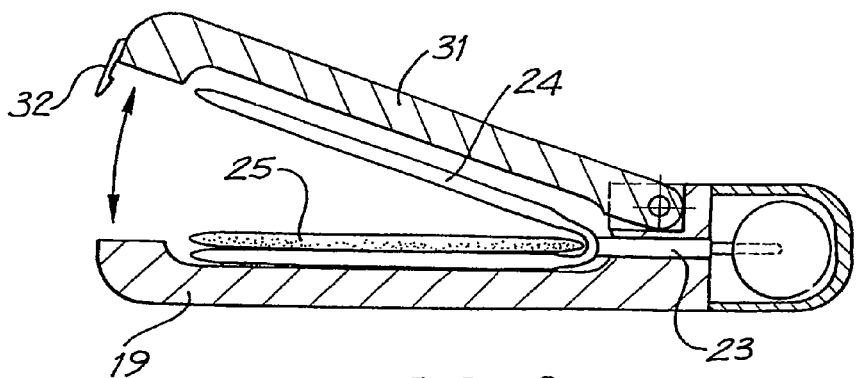
FIG. 8 is a cross-sectional elevation similar to FIG. 7, showing the apparatus in an open position.

As shown in FIG. 8, a side wall 31 may be hingedly opened from the housing 19. A fastener 32 is used to fasten the side wall 31 in a closed configuration when required. This hinged arrangement allows convenient access to the bag 25 for replacement of liquid or replacement of the bag. Moreover, the side wall 31 need not be sealed against the housing with gas seals, allowing facile design of the housing.

Other embodiments of the present invention will also be readily apparent to the person skilled in the art. For example, the chamber may include one or two internal diaphragms having a flexible membrane, the membrane(s) being in contact with the flexible bag. When the diaphragm is pressurized by a source of gas, it expands, thereby causing the membrane to exert a pressure on the exterior walls of the flexible bag. This and other embodiments are contemplated within the scope of the present invention.

EXAMPLES

An apparatus according to the second form described above was used to dispense liquid from a Baxter bag in two separate runs. In each run, the bag size was 50 mls and the pressure regulator was set to deliver 41.5 kPa of pressure from the gas cylinder. The amount of liquid dispensed from the bag was measured at one minute intervals.

Figure 10:
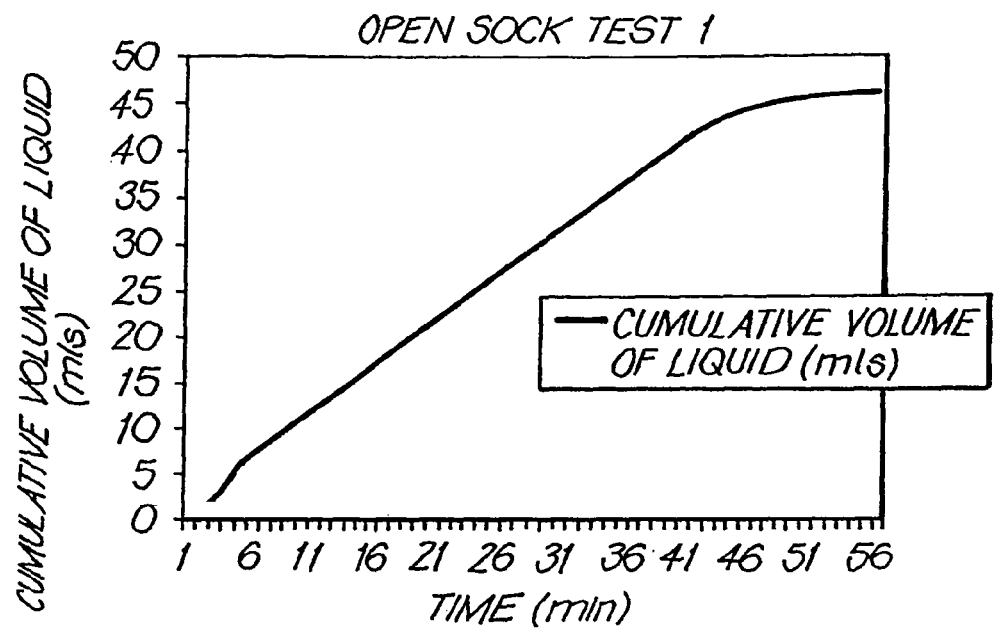
FIG. 10 is a graph displaying the results of a first liquid dispensing test performed on the apparatus shown in FIG. 5.
Figure 11:
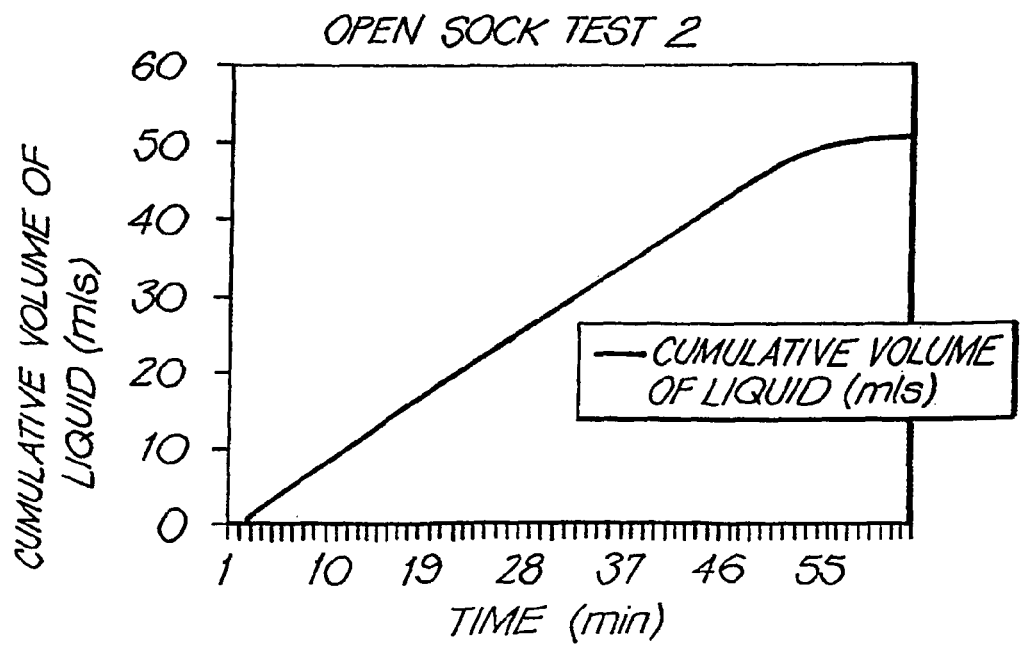
FIG. 11 is a graph displaying the results of a second liquid dispensing test performed on the apparatus shown in FIG. 5.

The results of these two separate runs are displayed graphically in FIG. 10 ("Open Sock Test 1") and FIG. 11 ("Open Sock Test 2").

The apparatus according to the present invention provides substantially linear flow of a liquid from a Baxter bag. In the case of this Example, the rate of flow is about 50 ml/hour. However, it will appreciated that other flow rates are, of course, possible, depending on the pressure of gas set by the pressure regulator.

The invention claimed is:

1. An apparatus for controlled rate dispensing of a liquid contained in a flexible bag, said apparatus including:
    a chamber configured to contain the flexible bag, the flexible bag having exterior walls and having an outlet conduit for the liquid;
    a source of gas arranged to provide gas to apply pressure to at least part of the exterior walls of the flexible bag in the chamber; and
    a pressure regulator positioned between the source of gas and the flexible bag, the pressure regulator being configured to continuously self-regulate a pressure of the gas supplied from the source of gas to continuously maintain the pressure of the supplied gas at a constant and predetermined level and so as to continuously maintain the pressure applied to the exterior walls of the bag at the constant and predetermined level throughout a duration of dispensing of the liquid,
    whereby the pressure applied to the exterior walls causes liquid to be dispensed from the flexible bag through the outlet conduit at a controlled rate.

2. The apparatus according to claim 1, wherein
    the chamber is a substantially gas-tight chamber comprising a liquid outlet configured to receive the outlet conduit and operable to seal the outlet conduit to the chamber,
    and
    the source of gas is operable to supply the gas under pressure to the interior of the chamber applying pressure to the exterior walls of the flexible bag.

3. The apparatus according to claim 1, further comprising an inflatable bladder, wherein the source of gas is connected to the inflatable bladder which is placed and operable such that, in use, the inflatable bladder is in contact with at least part of an exterior wall of the flexible bag.

4. The apparatus according to claim 3, wherein the inflatable bladder comprises an inflatable sock positioned and operable to wrap around at least part of the flexible bag.

5. The apparatus according to claim 3, wherein the pressure regulator is operable to regulate a flow of gas from the source of gas into the inflatable bladder.

6. The apparatus according to claim 1, wherein the source of gas comprises a pressure vessel of pre-compressed gas.

7. The apparatus according to claim 6, wherein the chamber has a cuboidal configuration with a depth significantly less than a length or width of the chamber, and wherein the pressure vessel and the pressure regulator are located alongside the chamber in a common housing arranged such that the pressure vessel and the pressure regulator are contained within the depth of the housing.

8. The apparatus according to claim 1, wherein the source of gas comprises a reservoir pressurised by a pump.

9. The apparatus according to claim 1, wherein the flexible bag is a medical supply bag of a type used to supply intravenous drip fluids for patients.

10. The apparatus according to claim 1, wherein the apparatus comprises a second chamber comprising the source of gas and the pressure regulator.

11. The apparatus according to claim 1, wherein the pressure regulator is a compression spring controlled piston device including at least one needle valve operable to regulate the pressure of the gas supplied from the source of gas.

* * * * *